United States Patent [19]
Gilbert

[11] 4,010,862
[45] Mar. 8, 1977

[54] FLUID CONTAINER HAVING SLIDING HANGER ON T-SHAPED SEALING BEAD
[75] Inventor: Dixie E. Gilbert, Orangeburg, N.Y.
[73] Assignee: Phillips Petroleum Company, Bartlesville, Okla.
[22] Filed: Nov. 7, 1974
[21] Appl. No.: 521,774

Related U.S. Application Data
[63] Continuation-in-part of Ser. No. 463,545, April 24, 1974, abandoned.
[52] U.S. Cl. .......................................... 215/100 A
[51] Int. Cl.² ........................................ B65D 23/00
[58] Field of Search .................. 215/100 A, 100 R; 248/359, 360; 222/180, 181; 206/806

[56] References Cited
UNITED STATES PATENTS

| | | | |
|---|---|---|---|
| 3,387,732 | 6/1968 | Jellies | 215/100 A |
| 3,686,379 | 8/1972 | Gilbert | 264/89 |
| 3,687,593 | 8/1972 | Gilbert | 18/5 B |

*Primary Examiner*—Donald F. Norton

[57] ABSTRACT

A fluid container designed to hang in an upside-down condition having a sealing bead in the form of a T, onto which a suspension tab is slidably affixed.

11 Claims, 8 Drawing Figures

FLUID CONTAINER HAVING SLIDING HANGER ON T-SHAPED SEALING BEAD

CROSS REFERENCE TO RELATED INVENTION

This is a continuation-in-part of application Ser. No. 463,545 filed Apr. 24, 1974, now abandoned.

BACKGROUND OF THE INVENTION

This invention relates to fluid containers designed to hang in an upside-down condition.

It is broadly known to provide plastic containers for use in dispensing intravenous fluids such as blood as is shown by Jellies, U.S. Pat. No. 3,387,732, issued June 11, 1968, which shows such a plastic bottle having an integrally molded hanger. It is also broadly known that oriented plastic containers have greater strength and durability as well as other desirable characteristics such as improved optical properties as shown for instance in Gilbert, U.S. Pat. No. 3,687,593, issued Aug. 29, 1972.

Since polymer at orientation temperature is difficult to mold, relatively complex molding techniques such as that disclosed in said Jellies patent present far greater problems when dealing with material at orientation temperature.

SUMMARY OF THE INVENTION

It is an object of this invention to produce a high strength plastic container having a separate suspension tab which is easily assembled; and it is a further object of this invention to provide a high strength fluid container having a suspension tab which can be folded into a recess so as to allow the container to set flat when in an upright position.

In accordance with the invention, a biaxially oriented container has a sealing bead in the form of a T onto which a separate suspension tab can be affixed in a sliding relationship.

BRIEF DESCRIPTION OF THE DRAWINGS

In the drawings which form a part hereof wherein like reference characters denote like parts in the various views.

DESCRIPTION OF THE PREFERRED EMBODIMENTS

Figure 1:
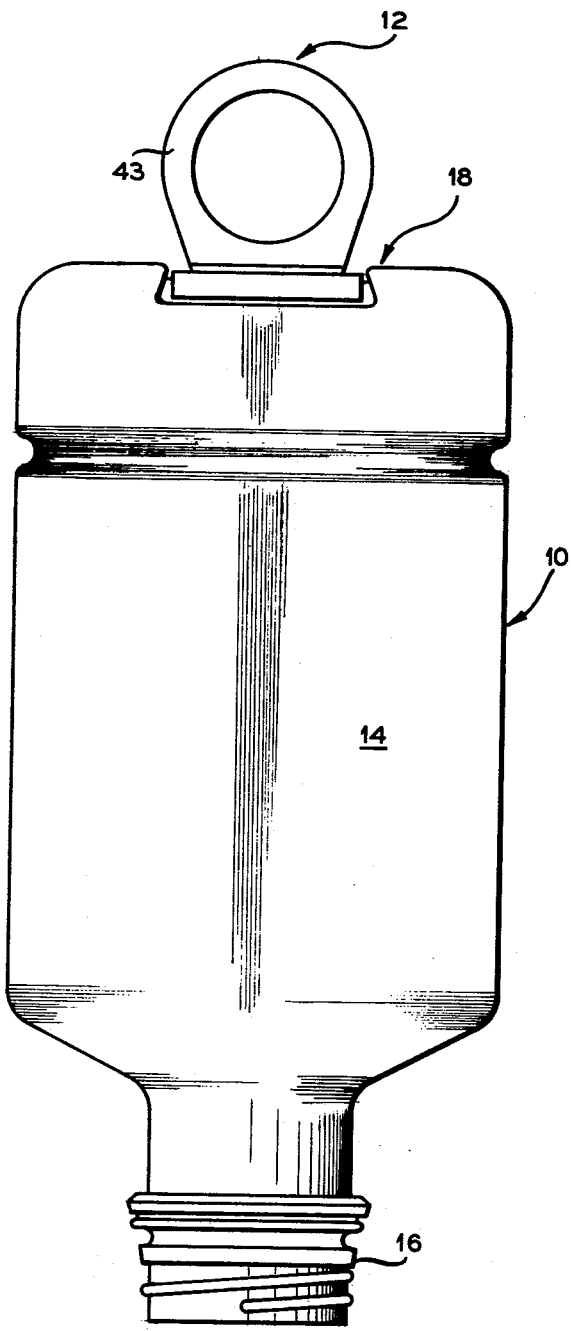
FIG. 1 is a side view of a high strength fluid container having a slidably attached suspension tab.

The container portion of the article of the invention can be made of any orientable thermoplastic material under conditions designed to give biaxial molecular orientation. Particularly suitable materials include polymers of at least one mono-1-olefin having 2-8 carbon atoms per molecule, preferably polymers of at least one monomer selected from the group consisting of ethylene, propylene, and 1-butene, most preferably polypropylene. Also amorphous polymers such as poly(vinyl chloride), polystyrene, styrene-acrylonitrile resins, butadiene-styrene containing polymers and the like can be used. The polymers are formed into the container portion of the article at orientation temperature where they are stretched both axially and circumferentially so as to give strengthening orientation in both directions.

By orientation temperature is meant that temperature at which polymers on stretching exhibit an increase in strength. For crystalline polymers such as polymers of mono-1-olefins having 2-8 carbon atoms per molecule, this temperature is generally within the range of 1° to 50° F, preferably 10° to 30° F below the crystalline melting point. Orientation temperature for amorphous polymers is generally 40° to 200° F, preferably 75° to 150° F below the homogeneous melt point.

The parison preforms from which the container portion of the article of the invention are made are preferably fabricated by extruding a continuous length of tubing which is thereafter cooled and cut up into individual work pieces. These parisons are thereafter heated while in the solid state, for instance, in an air oven, to orientation temperature. While at this temperature, the parisons are stretched longitudinally to impart orientation in one direction and then expanded to cause the parison to thus conform to the shape of the mold walls. The resulting article is biaxially oriented and has the high strength associated with orientation and further in the case of materials such as polypropylene, has high clarity. The parisons at orientation temperature have the general physical appearance of solid material and normally crystalline polymers are in a still partially crystalline state at which temperature they are not easily sealable. For this reason it has been found that a better seal can be made if a small bead is formed along the seal line.

In accordance with this invention the articles are formed having a large T-shaped bead along the sealing line which does not interfere with obtaining a seal under the adverse conditions inherent in the production of oriented articles and yet provides a means by which a suspension tab can easily be slid onto the container portion of the article.

The suspension tab can be made of the same or different material and need not be oriented. One suitable way to form the suspension tab is to injection mold same. A particularly suitable material for the tab is polypropylene because it has a capability of providing an excellent integral hinge to allow the suspension tab to be folded. Any of the plastic materials listed hereinabove for use in fabricating the container portion of the article can also be used. The suspension tab can be made of metal or other materials, but a plastic such as polypropylene is preferred.

Articles in accordance with the invention can be made in any desired size from about 29 ml to about 3800 ml or more (about one ounce to one gallon or more), but will generally be from 500 ml (about one pint) to 1500 ml.

In one embodiment, the T-shaped bead will be molded with thickened portions at each end on a cross bar portion thereof so as to provide a resistance to the tab being slid off after once installed on the container portion of the article.

One side of the bottom of the article is recessed so as to allow the tab to be folded down. It is essential that there be at least three flat portions spaced about the bottom of the container and that at least one be one each side of the recess into which the tab is folded. It is further essential that the T-shaped bead be within a longitudinal recess at least as deep as the height of the bead and that at least one of the flat portions be on each side of the recess so that the article can set flat when the tab is folded back. The bead must be large enough to be firmly held by the tab. Generally it will have a total height of 0.15–0.5 inch, preferably 0.15 to 0.30 inch. By height is meant the vertical height of the stem plus the thickness of the bar forming the T.

Referring now to the figures, particularly FIG. 1, there is shown an article in accordance with the invention having a container portion 10 and a suspension tab portion 12. The container portion has side walls 14, neck portion 16 and a bottom portion designated generally by reference character 18 to which the suspension tab is affixed as is shown hereinafter.

Figure 6:
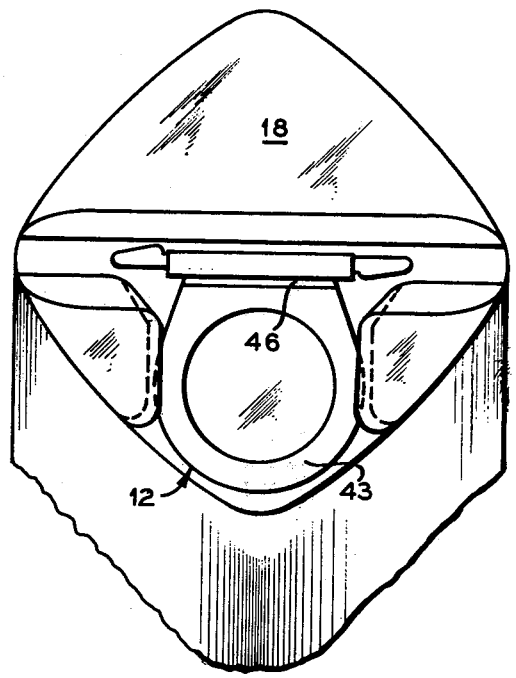
FIG. 6 is a perspective view showing the tab folded into a recess so as to allow the article to set flat in an upright position.
Figure 2:
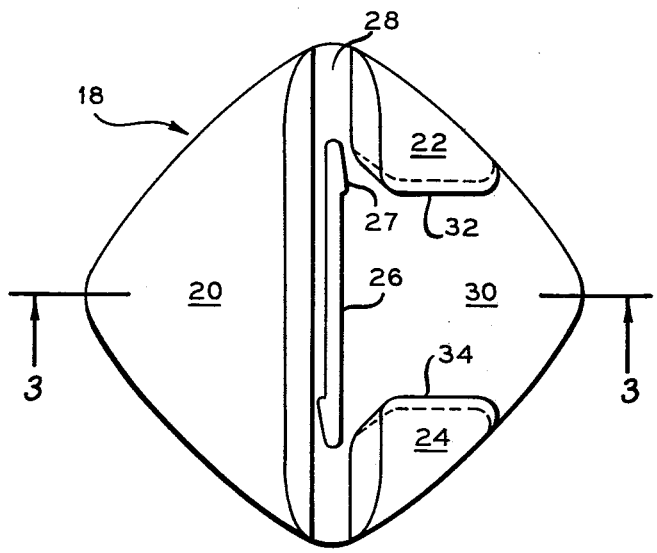
FIG. 2 is a bottom view of the article of FIG. 1.

FIG. 2 shows a view of bottom 18 showing flat portions 20, 22 and 24 on which the bottle can rest in a right-side-up condition. T-shaped sealing bead 26 having a boss at each end thereof is located within longitudinal recess 28. At right angles to the longitudinal recess is tab receiving recess 30. Flat portions 22 and 24 are undercut at portions 32 and 34 so as to allow for suspension tab 12 to be folded down and locked in a flat condition as shown in FIG. 6.

Figure 3:
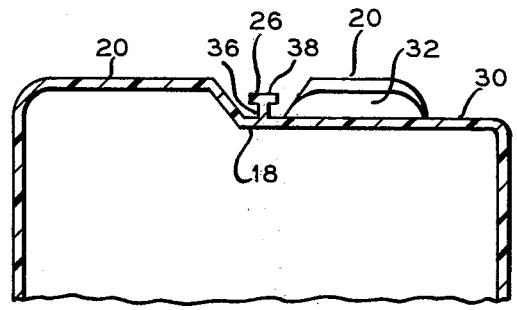
FIG. 3 is a view along section line 3—3 of FIG. 2.

FIG. 3 shows in greater detail T-shaped bead 26 which is connected to the bottom 18 of the container portion by longitudinal stem 36. As can be seen, the severing bead has a cross bar 38 which forms the T-shape.

Figure 4:
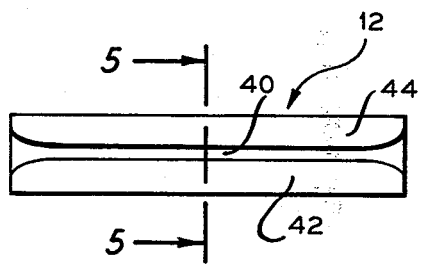
FIG. 4 is a view of the separate suspension tab member.
Figure 5:
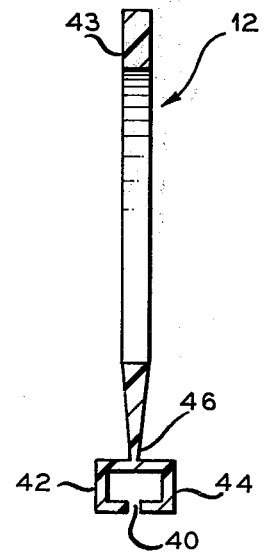
FIG. 5 is a cross-sectional view along section line 5—5 of FIG. 4.

FIGS. 4 and 5 show in detail a suspension tab 12 which has a slot 40 adapted to slidably engage cross bar 38, which slot is formed by downwardly and inwardly projecting members 42 and 44. Integral hinge 46, which is a constricted area between hanger 43, in the form of a ring, and members 42 and 44, allows the tab to be folded.

Tab 12 was formed separately and affixed to the container portion of the article by being slid over T-shaped sealing bead 26. After the tab has been slid onto the T-shaped sealing bead, it is held in place by a boss 27 (see FIG. 2) located at each end of the sealing bead. The tab can then be disposed in the open position as shown in FIG. 1 so that the bottle may be hung in an upside-down condition, or the tab may be locked into the undercuts at points 32 and 34 so that the bottle may set flat in an upright condition.

Figures 7, 8:
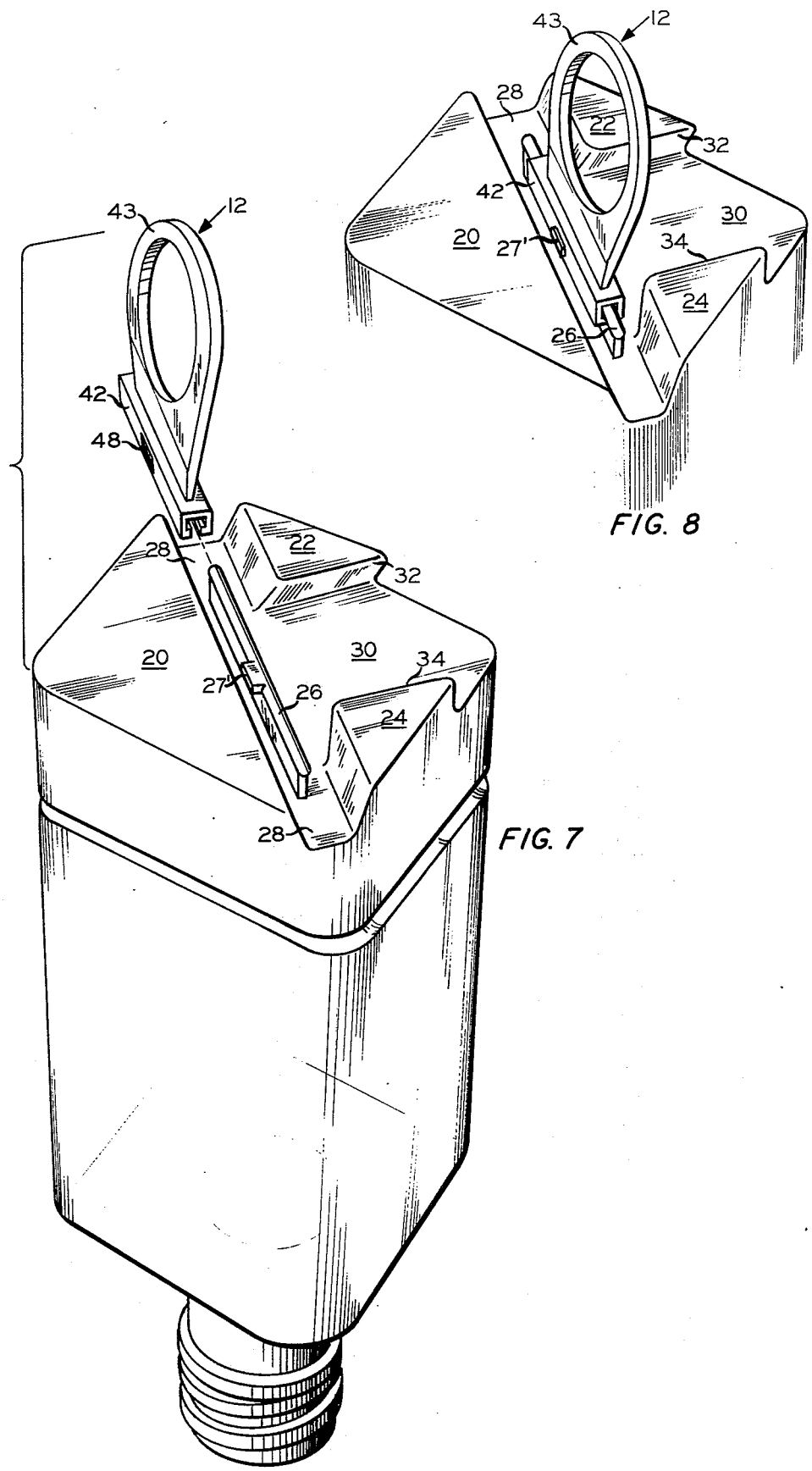
FIG. 7 is a perspective view showing an alternate embodiment of the invention with the tab detached.
FIG. 8 is a view similar to FIG. 7 with the tab attached.

FIG. 7 shows another embodiment wherein a boss 27' is provided between the ends, preferably in the center, of the bead 26. Alternatively, bead 26 can have 2, 3 or more bosses 27'. FIG. 7 shows a tab having opening 48 to receive boss 27'. FIG. 8 shows the tab locked into place. Alternatively member 42 can have a recess on the inside instead of hole 48 to serve as a means to cooperate with said boss 27'. By making the edges of boss 27' square, it is still easy to slip the tab on because of the sloping entrance between members 42 and 44, but is difficult to remove once boss 27' is fitted into hole 48.

EXAMPLE

Polypropylene homopolymer having a density of 0.905 (ASTM D-1505-63T) and a melt flow of 2 (ASTM D-1238-62T, Cond. L), and a crystalline melting point of about 340° F was extruded into tubing having an outside diameter of 1.375-inches and a wall thickness of 0.190-inch. The tubing was cooled to room temperature and cut into 5-inch long blanks. These blanks were placed in a heating chamber and heated to orientation temperature. Thereafter they were stretched longitudinally and mold halves closed thereupon, each mold having sealing and severing members having a forwardmost projection thereof in the form of a severing blade; immediately adjacent thereto these mold halves had a cross bar-forming cavity and a flat stem forming surface so as to form a configuration such as shown in FIGS. 2 and 3. The parison was expanded out circumferentially to form a biaxially oriented hollow bottle having a T-shaped sealing bead formed by opposed walls of the parison which were pressed together by the mold halves closing. The cross bar had a lateral dimension of 0.130 inch. and the stem a lateral dimension of 0.036 inch. The length of the stem and cross bar was approximately 2 inches. The distance between bosses at each end thereof was approximately 1-7/16-inches. The depths of the longitudinal recess and the tab forming recess were each approximately 11/32 -inch. The total height of the bead was about 0.2-inch.

A separate suspension tab was injection molded from polypropylene, said tab having a configuration such as that shown in FIGS. 4 and 5. The tab was then slid onto the T-shaped sealing bead to form the completed article. The article was filled with water, capped, and was found to be able to withstand a drop stress of greater than 25 foot pounds (the weight of the water in pounds mulitplied times the height in feet).

While this invention has been described in detail for the purpose of illustration, it is not to be construed as limited thereby, but is intended to cover all changes and modifications within the spirit and scope thereof.

What is claimed is:

1. A hollow article capable of sitting flat in an upright condition or being suspended in an upside-down condition comprising:
    a biaxially oriented container portion having a neck, side walls, and a bottom, which bottom has at least three flat portions spaced around said bottom;
    a longitudinal recess passing through a center axis of said article, said recess having a longitudinal T-shaped sealing bead therein comprising a longitudinal cross bar having a boss at each end and a longitudinal stem connecting said cross bar with said bottom wall in said recess, at least one of said flat surfaces being on each side of said longitudinal recess;
    said bottom further having a tab receiving recess at right angles to said longitudinal recess, one of said flat surfaces being on each side of said tab receiving recess, said tab receiving recess being so contoured as to form an undercut between said flat surfaces on each side of said tab receiving recess and a portion of said bottom within said tab receiving recess;
    and a suspension tab slidably affixed to said T-shaped sealing bead, said tab having downwardly and inwardly projecting members which form a slot, said tab further having a hanger portion having a hole therein and an integral hinge adjacent said downwardly and inwardly projecting members and connecting same with said hanger portion.

2. An article according to claim 1 wherein said biaxially oriented container portion is made of polypropylene.

3. An article according to claim 1 wherein said bottom has three flat surfaces, one of which constitutes substantially the entire portion of the bottom on a side of said longitudinal recess opposite said side which has said tab receiving recess.

4. An article according to claim 1 wherein said suspension tab is made of polypropylene.

5. An article according to claim 1 wherein said bead has a height within the range of 0.15 to 0.50 inch.

6. An article according to claim 1 wherein said article is a container for intravenously administered fluids.

7. An article according to claim 6 wherein said container is made of polypropylene, said bottom has three flat surfaces, one of which constitutes substantially the entire area on a side of said longitudinal recess opposite said side having said tab receiving recess and said suspension tab is made of polypropylene.

8. A plastic container having an integral base, an elongated, inverted, substantially T-shaped rib integral with and depending from said base, and a loop integrally joined to an elongated, substantially C-shaped bar complementary to and slidably affixed onto said T-shaped rib, said T-shaped rib having a transverse lug extending therefrom for locking said bar onto said rib.

9. A plastic container having an integral base, an elongated, inverted, substantially T-shaped rib integral with and depending from said base, and a loop integrally joined to an elongated, substantially C-shaped bar complementary to and slidably affixed onto said T-shaped rib, said rib having a transverse lug extending therefrom and said bar having an aperture therein complementary to and receiving said lug to lock said bar on said rib.

10. A hollow article capable of sitting flat in an upright condition or being suspended in an upside-down condition comprising:
    a biaxially oriented container portion having a neck, side walls, and a bottom, which bottom has at least three flat portions spaced around said bottom;
    a longitudinal recess passing through a center axis of said article, said recess having a longitudinal T-shaped sealing bead therein comprising a longitudinal cross bar having at least one boss at a point between the ends thereof and a longitudinal stem connecting said cross bar with said bottom wall in said recess, at least one of said flat surfaces being on each side of said longitudinal recess;
    said bottom further having a tab receiving recess at right angles to said longitudinal recess, one of said flat surfaces being on each side of said tab receiving recess, said tab receiving recess being so contoured as to form an undercut between said flat surfaces on each side of said tab receiving recess and a portion of said bottom within said tab receiving recess;
    and a suspension tab slidably affixed to said T-shaped sealing bead, said tab having downwardly and inwardly projecting members which form a slot, said tab further having means to cooperate with said boss to hold said tab on said bead and a hanger portion having a hole therein and an integral hinge adjacent said downwardly and inwardly projecting members and connecting same with said hanger portion.

11. An article according to claim 10 wherein said bead has one generally centrally disposed boss and said means to cooperate with said boss is a hole in said downwardly and inwardly extending member of said tab.

* * * * *